(12) United States Patent
Coates (10) Patent No.: US 8,968,264 B2
(45) Date of Patent: Mar. 3, 2015

(54) COMFORT DIAPER ASSEMBLY

(75) Inventor: Fredrica V. Coates, Winston-Salem, NC (US)

(73) Assignee: Tailored Technologies, Inc., Winston-Salem, NC (US)

( * ) Notice: Subject to any disclaimer, the term of this patent is extended or adjusted under 35 U.S.C. 154(b) by 459 days.

(21) Appl. No.: 13/387,373

(22) PCT Filed: Jul. 27, 2010

(86) PCT No.: PCT/US2010/043358
§ 371 (c)(1),
(2), (4) Date: Jan. 27, 2012

(87) PCT Pub. No.: WO2011/014495
PCT Pub. Date: Feb. 3, 2011

(65) Prior Publication Data
US 2012/0123364 A1    May 17, 2012

Related U.S. Application Data

(60) Provisional application No. 61/273,059, filed on Jul. 30, 2009.

(51) Int. Cl.
*A61F 13/15* (2006.01)
(52) U.S. Cl.
USPC ............ 604/385.14; 604/385.19; 604/385.15; 604/385.201; 604/385.24; 604/385.25; 604/385.28
(58) Field of Classification Search
USPC .................. 604/367, 385.24, 385.25, 385.28, 604/385.201, 385.14, 385.19, 385.15
See application file for complete search history.

(56) References Cited

U.S. PATENT DOCUMENTS

| | | | |
|---|---|---|---|
| 4,128,686 A * | 12/1978 | Kyle et al. | 428/219 |
| 4,961,736 A | 10/1990 | McCloud | |
| 5,137,526 A | 8/1992 | Coates | |
| 5,409,476 A | 4/1995 | Coates | |
| 5,707,364 A | 1/1998 | Coates | |
| 5,722,127 A | 3/1998 | Coates | |
| 5,814,037 A | 9/1998 | Coates | |
| 6,254,583 B1 | 7/2001 | Coates | |
| 6,895,603 B2 | 5/2005 | Coates | |
| 6,926,705 B1 | 8/2005 | Coates | |
| 7,166,095 B1 | 1/2007 | Coates | |
| 2002/0143316 A1 | 10/2002 | Sherrod et al. | |
| 2007/0239132 A1 | 10/2007 | Mishima | |

FOREIGN PATENT DOCUMENTS

WO    WO 2007/021734 A2    2/2007

OTHER PUBLICATIONS

International Search Report dated Sep. 17, 2010 for International Patent Application No. PCT/US2010/043358.

* cited by examiner

*Primary Examiner* — Jacqueline F. Stephens
(74) *Attorney, Agent, or Firm* — Shumaker, Loop & Kendrick, LLP (57) ABSTRACT

A diaper assembly 2 includes a diaper garment 10 and a fluid absorbent pad 60. The diaper garment 10 has an outer shell 12 from which a sling 20 is suspended. The sling 20 is fluid resistant and has front and rear pockets 34, 36 into which opposite ends of the fluid absorbent pad 60 can be inserted. The front pocket 34 is formed by fluid resistant shield 50 that is surrounded on three sides by gussets 40, 42 that are more skin friendly than the shield 50. Multilayer pads 60 can be carried by the sling 20.

27 Claims, 11 Drawing Sheets

COMFORT DIAPER ASSEMBLY

This application claims priority to U.S. Provisional Patent Application No. 61/293,059 filed on Jul. 30, 2009, the entirety of which is hereby incorporated by reference herein.

BACKGROUND OF THE INVENTION

1. Field of the Invention

This invention related to undergarments, and particularly to diapers or nappies and fluid absorbent pads used with diapers. More specifically, this invention relates to reusable diapers in which reusable fluid absorbent pads may be employed. Furthermore, this invention relates to diapers and diaper assemblies in which the components of the assembly function together to provide sufficient comfort and protection to the wearer both for infants and for adults.

2. Description of the Prior Art

Protective underwear having a waterproof or water-resistant sling is shown in U.S. Pat. No. 5,137,526; U.S. Pat. No. 5,409,476; U.S. Pat. No. 5,707,364; U.S. Pat. No. 6,254,583; U.S. Pat. No. 5,722,127; U.S. Pat. No. 6,895,603; and U.S. Pat. No. 6,926,705. U.S. Pat. No. 5,814,037 shows a protective undergarment with a suspended pocket-sling. Front and rear ends of these slings are joined to an outer shell so that the sling can isolate body fluids and fecal matter from the outer shell. A suspended pocketed sling shown in U.S. Pat. No. 6,895,603 is formed by folding front and rear sections of a rectangular fabric about fold lines extending transverse to the major or longitudinal dimension of the rectangular fabric, so that overlapping portions of the rectangular fabric form fore and aft pockets. Elastic is placed along side edges to recess and cup the entire frontal portion of the sling to better fit the wearer's anatomy. Stitching along sides of the end edges of the pocket holds the three plies of the S-folded fabric construction together. A rectangular pocket opening is thus formed by the transverse fold lines and the longitudinal edges of the rectangular fabric. Remote ends of this pocketed sling can then be attached or stitched to the outer shell, which may be in the form of a pant or a diaper. The sling can hang freely from the opposite ends of the garment, and the absence of stitching between the sling and the garment in the area of the pocket eliminates a leakage path. A disposable pad, either reusable or disposable can be fitted in the pocket, with the ends of the pad held by the fore and aft overlapping or S-shaped sections at opposite ends of the rectangular pocket opening. Although this rectangular pocket can provide a pocket of sufficient volume to collect bodily wastes, and an absorbent pad can be held in place within the pocket, the rectangular opening does not naturally conform to pubic area of the wearer. The exposed material along the crease lines formed by the transverse fold can become soiled compromising the effectiveness of the protective undergarment. This is especially a problem along the front of the undergarment when used for males, especially small boys, because the straight edge of the rectangular opening wets easily.

In some prior art undergarments formed with S-pockets having rectangular edges, elastic encircles the rectangular sling opening. This elastic pulls material inward and can cause the pocket opening to take on an oval shape with curved front and rear openings. However, this effect of the elastic reduces the size of the pocket opening and provides less, not more, exposure of a disposable pad. This effect thus exposes more of the layer of the sling adjacent to the wearer to the pubic area and increases the area that can be wetted, especially for males. This ovaling effect thus reduces the effectiveness of S-pocket garments formed by a rectangular fold line.

U.S. Pat. No. 5,707,364 discloses another type of recessed pocket, in which a replaceable pad may be positioned. A recessed pocket formed according to U.S. Pat. No. 5,707,364 includes drop strips on either side of the recessed pocket. These drop strips provide depth to the pocket and they are stitched to an absorbent channel) at the base of the drop strips. As disclosed in U.S. Pat. No. 5,707,364, absorbent pads fit between the drop strips, and it is the added depth that is primarily relied upon to retain the removable absorbent pads in place. Some embodiments depicted therein include elastic strips extending over the pads between the drop strips to provide additional restraint. A bumper strip extends across the front of the sling, and that sling is free to float relative to the outer shell of the protective undergarment or diaper shown therein. The sling formed by the drop strips and the channel are joined to the bumper by an arcuate seam. U.S. Pat. No. 5,707,364 refers to this as recessing and pocketing, but the pocket referred to therein is in the middle of the sling and not at its ends. There is no pocket above the acruate seam, because that seam extends through both the drop strips and the channel. Thus there is no S-pocket formed above seam for receiving or retaining an end of a disposable pad either at the front or rear of the garment, nor does the arcuate seam provide a capability to retain a pad of any kind.

International Publication WO 2007/021734 does disclose slinged undergarments in which the sling has arcuate pockets, but that configuration sacrifices the wearer's comfort to prevent soiling the garment.

SUMMARY OF THE INVENTION

The invention disclosed herein not only provides a diaper garment that can minimizes soiling of the garment, but also enhances the comfort of the wearer by not exposing the wearer to abrasive surfaces or components of the diaper that must be constructed of fabrics or materials that are not skin friendly and can therefore cause discomfort. Furthermore, the diaper assembly depicted herein, reduces the bulk of the diaper assembly and the fluid absorbent pad used therein, so as to reduce this source of potential discomfort to the wearer. Furthermore, this diaper assembly minimizes collection or retention of moisture on the skin, and transfers much of this moisture into the pad, positioned in the diaper sling. Comfort is provided without sacrificing protection.

A diaper or nappy assembly according to one aspect of this invention includes a fluid absorbent pad and a diaper garment. The diaper garment has an outer shell including fasteners for securing the diaper garment to a wearer. The diaper garment also includes a fluid resistant sling secured at a front end to the outer shell and at a rear end to the outer shell. The sling is free from the outer shell between the front end and the rear end. The fluid absorbent pad is carried by and can be removed from the fluid resistant sling. The sling has a front pocket and a rear pocket. Opposite ends of the fluid absorbent pad can be inserted into the front and rear pockets of the sling. A rear fabric layer, softer to the touch than the fluid resistant sling, covers the rear pocket. A top fabric gusset and two side fabric gussets, each formed from a material softer to the touch than the fluid resistant sling, are secured to a fluid resistant front shield to cover the front pocket and to secure the sling at the front end to the outer shell. These gussets surround the fluid resistant shield on three sides, and the front pocket provides greater moisture leakage protection than the rear pocket while the gussets are provide comfort to a wearer's skin.

One advantage of the diaper assembly according to this invention is that it can use a multilayer fluid absorbent pad that can be carried by the diaper sling. The fluid absorbent pad comprises a reusable fabric pad having three side by side sections joined by a flexible strip on each side of a central section attaching the central section to sections on each side thereof so that the sections are foldable into overlapping relationship for insertion into the sling. Each section of the fluid absorbent pad has an overlock stitch extending along opposite sides between a top and bottom end of the pad. The overlock stitch stiffens the periphery of each section along opposite sides thereof so that the sections will retain their shape and fold more easily for a comfortable fit and will not bunch up in the sensitive groin area when worn. The pads will be easier to handle and will unfold easily for cleaning.

DETAILED DESCRIPTION OF THE PREFERRED EMBODIMENTS

Figure 1:
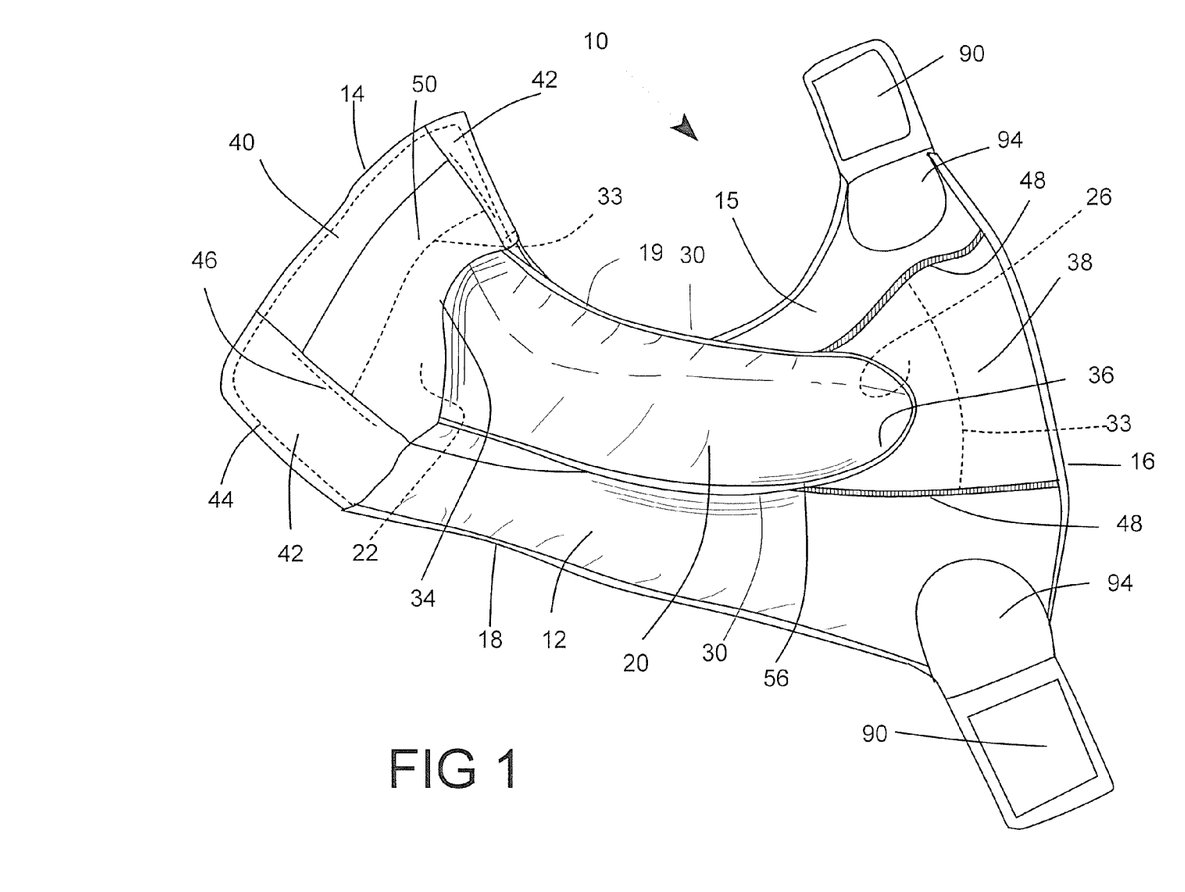
FIG. 1 is a three dimensional view of a diaper garment according to this invention.
Figure 2:
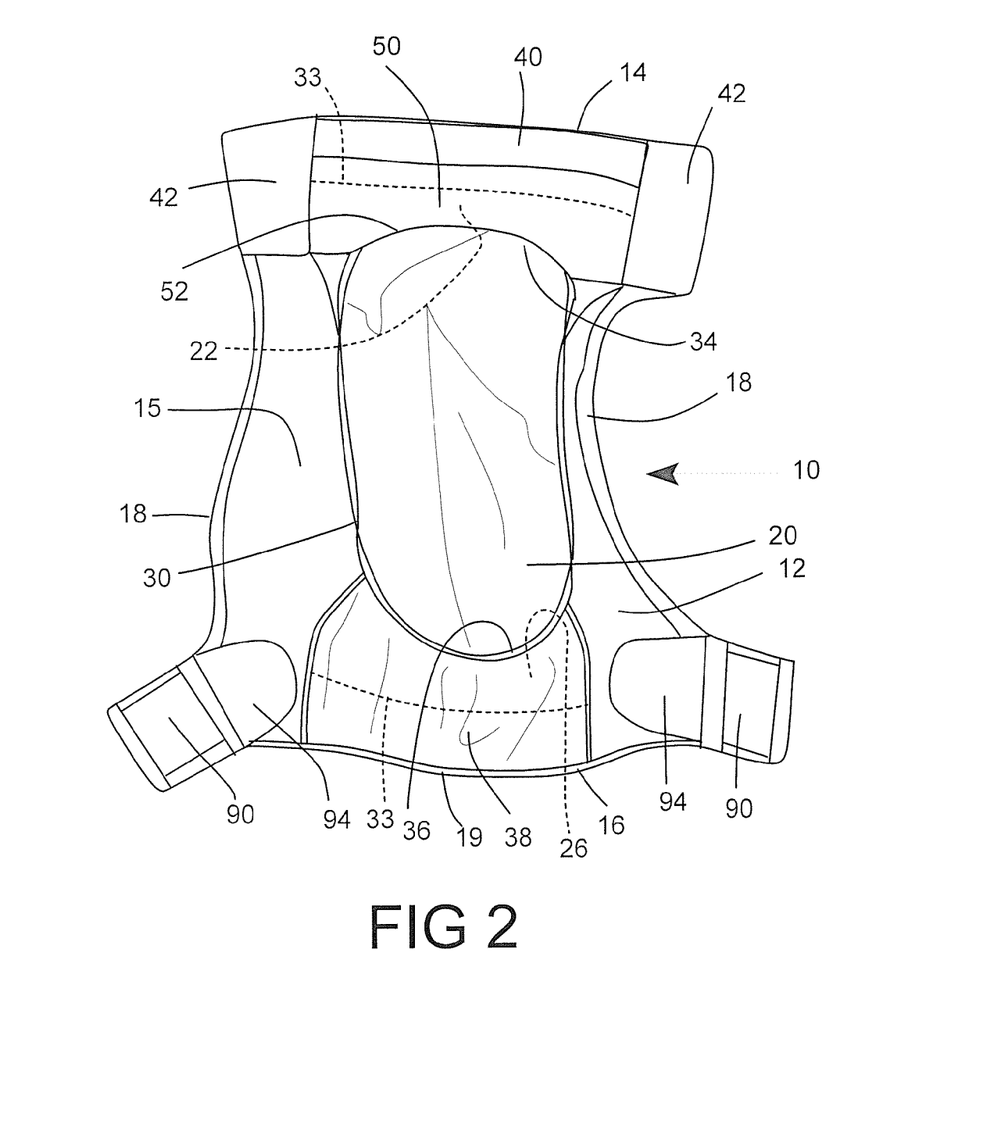
FIG. 2 is two dimensional view of the diaper garment shown in FIG. 1, showing the general shape of the sling opening into which a fluid absorbent pad is to be inserted.
Figure 3:
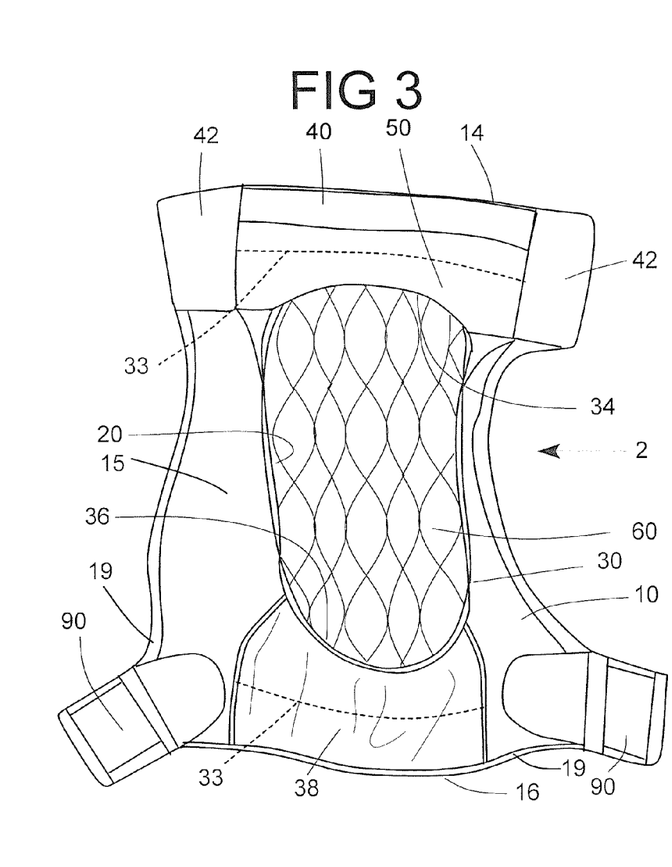
FIG. 3 is a view of a diaper assembly according to this invention showing a fluid absorbent pad inserted into the sling opening as shown in FIG. 2.
Figure 4:
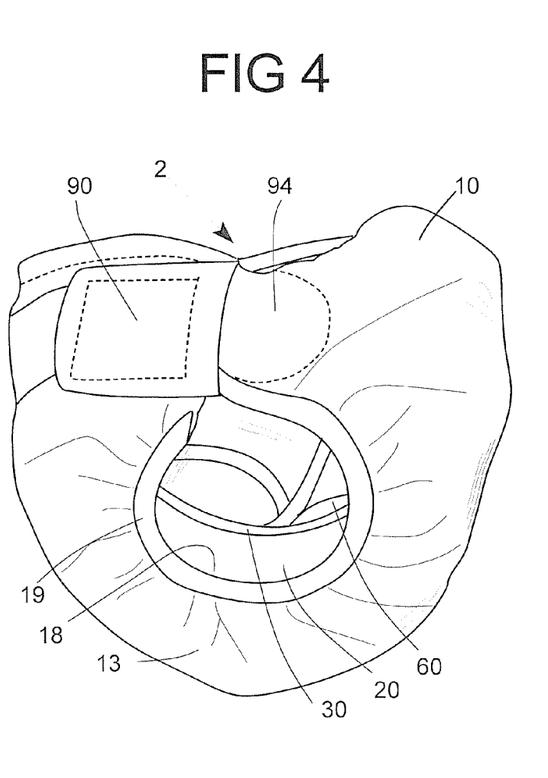
FIG. 4 is a view of the diaper assembly of FIGS. 1-3 showing how the diaper garment is fastened for wearing.

The comfort diaper or nappy assembly 2 according to this invention comprises a diaper garment 10 containing a fluid absorbent pad 60. The diaper garment 2 is shown in FIGS. 1 and 2, and the diaper assembly, including the fluid absorbent pad 60 is shown in FIG. 3. FIGS. 1-4 show the diaper assembly 2 and the diaper garment 10 in an open configuration and FIG. 4 shows the diaper assembly 2 in its closed configuration as it would be worn. In the preferred embodiments, both the diaper garment 10 and the fluid absorbent pads 60 are reusable.

The comfort diaper garment 2 has an outer shell 12 on which a sling 20 is mounted. In the preferred embodiment of this invention, the outer shell 12 has two layers. A soft outer layer 13 surrounds an inner, anchor layer 15. Preferably the inner anchor layer 15 is fabricated from a fluid resistant or waterproof material, such as a surgical garment material of polyester woven tightly enough to be waterproof or a polyurethane coated polyester. Another alternative would be wool, although a number of different fluid resistant or waterproof materials would be suitable Materials such as GORE-TEX could be employed. GORE-TEX is a registered trademark of W.L. Gore & Associates. The outer layer 13 can be formed of a material, such as a cotton jersey or knit or woven materials, or blends of materials and micro fibers among others, that is softer or more decorative than the anchor layer 15, but the inner, anchor layer 15 will protect the outer layer 13 from being wetted or stained during use. The outer layer 13 is joined to the inner, anchor layer 15 around the periphery of the outer shell 12, and an elastic border 19 around the sides will form leg holes or openings 18 when the diaper garment 10 is worn in the configuration of FIG. 4.

The sling 20, into which the fluid absorbent pad 60 can be inserted, is also formed of a fluid resistant or waterproof material, such as a surgical garment material of polyester woven tightly enough to be waterproof or a polyurethane coated polyester. Another alternative would be wool, although a number of different fluid resistant or waterproof materials would be suitable. Materials such as GORE-TEX would also be suitable. GORE-TEX is a registered trademark of W.L. Gore & Associates. The sling will contain most if not all of the fluid or excrement deposited during use of the diaper assembly 2. Together with the inner or anchor layer 15 and outer layer 13 of the shell 12, the sling 20 will provide double protection against leakage. The sling 20 will be located on the inside of the outer shell 12, and since the sling 20 is fabricated from a fluid resistant material, it will not be as skin friendly or as soft to the touch, as might be desired. As shown in FIGS. 1 and 2, the fluid resistant sling 20 is suspended from the outer shell 12 only at the front sling end 22 and the rear sling end 26. The sling side edges 30 between opposite ends are not attached to the shell side edges 18. Thus the sling 20 is largely separate from the shell 12. This separation along the sides will allow the sling 20 to fit tightly, but comfortably, around the groin area, while the shell side edges 18 will form leg openings, as shown in FIG. 4, which will also fit tightly and comfortably to form a further barrier against leakage.

The sling 20 forms a front pocket 34, which will receive and retain one end of a fluid absorbent pad 60, and a rear pocket 36 which will receive and retain the opposite end of pad 60. Both the front pocket 34 and the rear pocket 36 are formed by folding forward, along crease lines 33, the respective sling end portions 22 and 26 so that the fluid resistant sling 20 will fold inwardly to extend over the top and bottom end surfaces of an absorbent pad 60 when inserted into the sling 20, thus holding the pad securely in place. The construction of the front pocket 34 will differ from the construction of the rear pocket 36, as will be discussed with reference to FIGS. 5-8.

Figures 7, 8A, 8B:
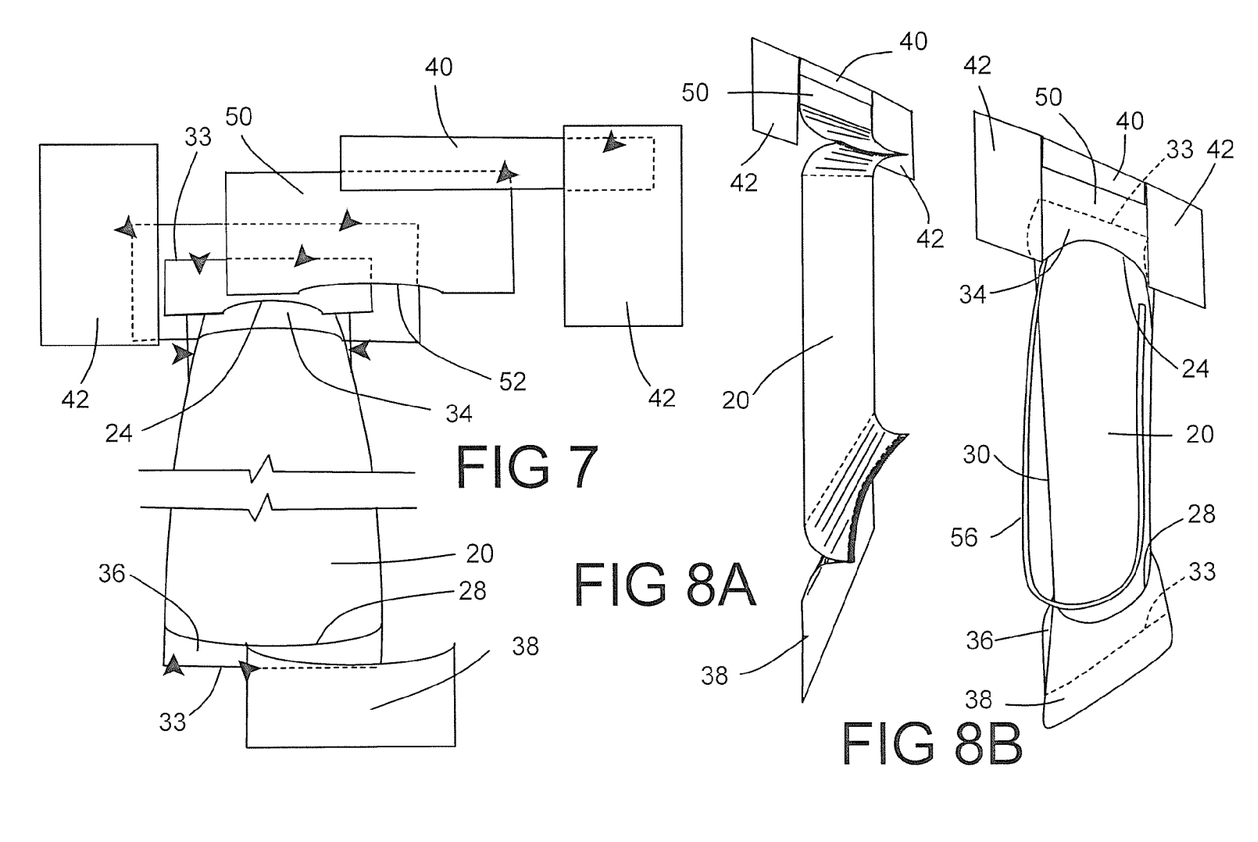
FIG. 7 is a view showing the manner in which the components of FIGS. 1-3 are positioned for assembly.
FIGS. 8A and 8B are views showing the assembly of the sling including attachment of the front gussets to the sling in one stage of assembly and formation of the sling pockets and attachment of the elastic to the sling subassembly.

Both the front pocket 34 and the rear pocket 36, as shown in FIGS. 2, 3 and 8B have an arcuate contour that will expose more of the fluid absorbent pad 60 along the centerline of the sling 20. The front pocket 34 is covered by a fluid resistant shield 50 extending on opposite sides of the centerline of the sling 20. The rear pocket 36 is covered by a rear fabric layer 38 that is constructed of a material that is softer to the touch, and therefore more comfortable than the fluid resistant material forming the front shield 50. Rear fabric layer 38 suspends the rear end of the sling 20 from the outer shell 12. The front pocket 34 will therefore provide more leakage protection than the rear pocket 36, and will be positioned where greater leakage protection is important. The sling 20 in the vicinity of the front pocket 34 will also be less likely to bunch up toward the sling centerline than with the sling 20 in the vicinity of the rear pocket 36. Fabric gussets, including a top gusset 40 and two side gussets 42 are stitched to the front, fluid resistant shield 50, reduce the size of exposure of the fluid resistant shield 50 to the wearer's skin. The fabric gussets 40 and 42 are softer to the touch, and therefore more comfortable. These gussets 40 and 42 are located in an area that will not normally be exposed to fluids or moisture, and the gussets will not adversely reduce the amount of leakage at the front of the sling 20.

Figure 5:
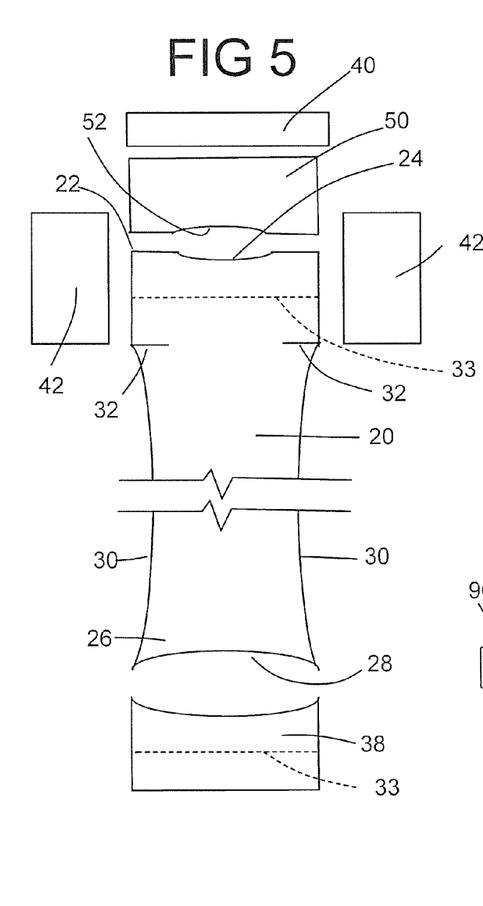
FIG. 5 is a view of the individual components forming the sling of the embodiments of FIGS. 1-3.
Figure 6:
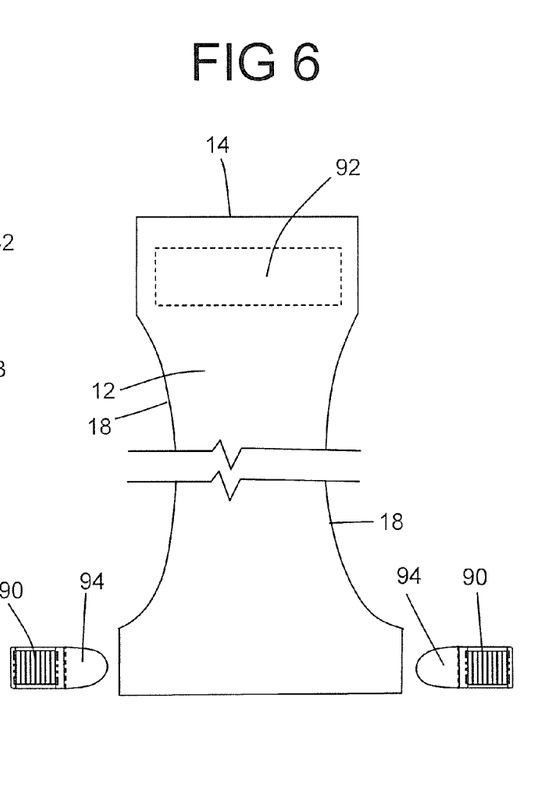
FIG. 6 is a view of the components of the outer shell to which the sling, formed from the components of FIG. 5, will be attached to form the diaper garment of FIGS. 1-3.

FIG. 5 shows the individual components that are assembled to form the subassembly containing the sling 20 and FIG. 6 shows components for assembling the outer shell 12. The break lines in FIGS. 5 and 6 show that the individual components are not necessarily to scale and have been somewhat exaggerated to better illustrate the components in a single figure. FIG. 7 shows the relationship of the sling components and FIGS. 8A and 8B illustrate intermediate steps in fabricating the sling subassembly prior to stitching the sling 20 to the outer shell 12. Sling 20 comprises an elongate, preferably fluid resistant, piece of material that has been cut to form arcuate end edges 24 and 28 and side edges 30, as best seen in FIG. 5. The front sling edge 24 is at least partially arcuate. A fluid resistant front shield 50 has an arcuate edge 52, which will ultimately be stitched to the sling front end 22, back to back as the two pieces of fabric enclose and encase ends of an elastic strip 56 when applied to sides 30 and along the arcuate sling edge 28. See FIGS. 8A and 8B. Shield 50 generally matches the front sling edge 24 on the front sling portion 22. As front shield 50 is stitched to front sling portion 22, the terminal ends of an elastic strip 56 are encased, leaving a smooth seam against the wearer. This front shield has an arcuate edge or contour 52 that generally matches the arcuate edge 24 on the sling 20, and the front shield 50 will be stitched to the front sling end 22 so that arcuate edges 24 and 52 will be joined together. A rear fabric layer 38, which is preferably softer and more friendly to the touch than the fluid resistant sling 20, will be joined to the sling rear end 26 along the rear arcuate sling edge 28.

The fluid resistant front shield 50 is flanked by three fabric gussets 40 and 42 that are fabricated from a material that is more friendly to the touch than the fluid resistant material from which the front shield is formed. The front shield 50 and the three gussets 40 and 42 form a front subassembly. In the preferred embodiment, the fabric gussets 40 and 42 can be fabricated from a material such as for example cotton jersey, and the fluid resistant front shield is fabricated from a material such as such as surgical garment material, wool or even coated materials such as GORE-TEX, which is a registered trademark of W.L. Gore 7 Associates. Top gusset 40 will be stitched to the top edge of the front shield 50. The two side gussets 42 will be stitched to the side of the front shield 50 and will also overlap side edges of the top gusset 40.

FIG. 7 shows the sling components also shown in FIG. 5. The relative position of the sling components as they are stitched together is shown in FIG. 7. The arrowheads in FIG. 7 show either that one component will overlap the component shown next to it or that show that the sling 20 is folded, for example along crease line 33, prior to being stitched to another sling component. The portion of the sling at the top in FIG. 7 is folded over along a crease line 33 to form the front pocket 34 before the other components are stitched to the sling 20. Similarly the rear sling end 26 is folded over adjacent sections of the sling 20, along crease line 33, to initially form the rear pocket 36 into which an end of the fluid absorbent pad 60 will be inserted. The rear pocket 36 will comprise an S-shaped pocket when viewed from the sides. The sling front end 22 is folded inwardly along opposite sides. With the folds formed in the sling 20 in this manner, the front shield 50 will be positioned over the folded front portion of the sling 20. Similarly the rear fabric layer 38 will be positioned over the folded rear portion of sling 20, it will overlay the rear of the sling and the rear pocket 36. As shown in FIG. 7, the top gusset 40 will be positioned over the front shield 50 and the side gussets 42 will be positioned and attached on opposite sides to the front shield 50 and over ends of the top gusset 40. When positioned in this manner, adjacent and overlapping sling components can be stitched or joined together to form a sling subassembly that can then be attached to the outer shell 10 at the front shell end 14 and the rear shell end 16. FIGS. 8A and 8B shows assembly steps if in fabricating the sling subassembly.

Components and subcomponents of the outer shell 12, to which the sling subassembly will be attached, are shown in FIG. 6. As previously discussed, the outer shell 12 has two layers, but since these two layers 13 and 15 have the same shape, they are not separately shown in FIG. 6 since the two layers 13 and 15 would have previously been joined or stitched to form the shell body shown in FIG. 6. Hook fasteners 90, along with auxiliary closing tabs 94 are stitched to opposite ends of the shell adjacent the shell rear end 16. The auxiliary closing tabs can be formed of a loop material and the hook fasteners 90 can be attached to these auxiliary closing tabs 94 during cleaning or storage to prevent the hook fasteners 90 from damaging the garment during handling. The hook fastener subassembly including hook fasteners 90 and auxiliary closing tabs 94 can be preassembled, as will be subsequently discussed, before this fastener subassembly is stitched to the outer shell 12. An elongate loop fastener 92 is stitched on the exterior or opposite side of the shell 12, and is shown in phantom in FIG. 6. The elongate loop fastener 92 will be attached near the front end 14 so that the hook fasteners 90 can engage any portion of the loop fastener 92 in the closed position shown in FIG. 4, so that the diaper will snugly fit wearer's of different sizes.

Figure 9:
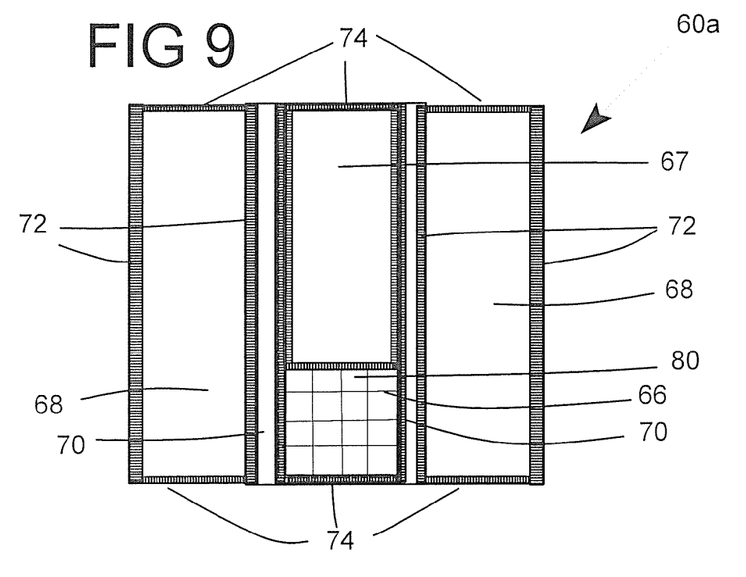
FIGS. 9 and 10 are views of opposite sides of one version of a reusable absorbent pad that can be employed to form the diaper assembly of this invention.
Figure 10:
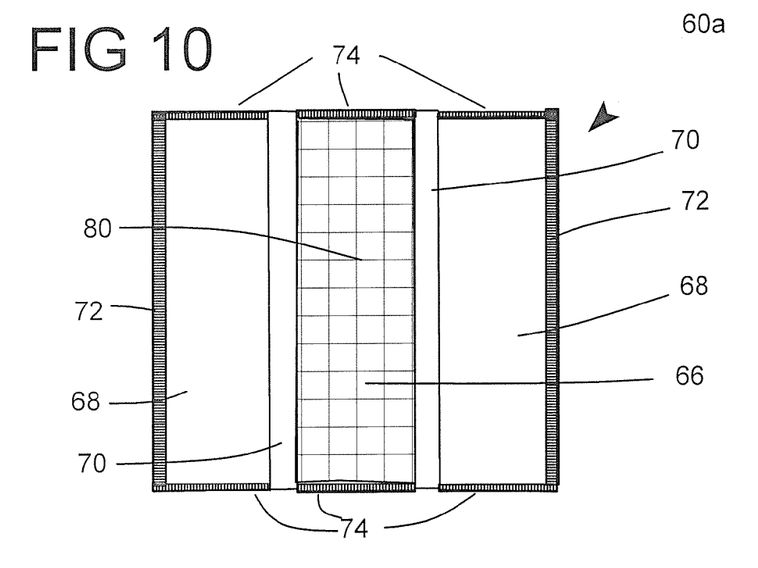

After the sling subassembly has been completed, the top gusset 40 and the side gussets 42 are attached to the outer shell 12 by a peripheral stitch 44 that extends around the upper sides and top of the garment as seen in FIG. 1. The gussets 40 and 42 are thus the primary means of attaching the sling 20 to the outer shell 12 along the front end 14 of the shell. An anchoring stitch 46 along the edge of the side gussets will then secure the front portion of the sling 20 to the outer shell. This anchoring stitch 46 can extend though the shell and through the loop fastener on the exterior of the diaper garment 10. This anchoring stitch 46 can also extend through the front shield 50. The rear sling end 26 can be stitched to the inner layer 15 at the rear end 16 of the diaper garment 10. An overlock stitch 48 secures the sides of the rear fabric member 38 to the sides forming the rear pocket 36 folded along crease line 33 at the rear end of sling 20. The diaper garment 10 is especially suited for use with a reusable or fabric fluid absorbent pad 60, which has sections that can be folded in overlying relationship prior to being inserted into the sling 20. Three different, representative versions of folding fluid absorbent pads 60*a*, 60*b* and 60*c* are shown in FIGS. 9-14. Each of these fluid absorbent pads comprises a trifold pad having a central pad section 66 flanked by two side pad sections 68. The sections 66, 68 forming these folded pads 60 are joined by flexible strips 70 that extend between opposite ends of the pad sections. Typically these flexible strips 70 are thinner than the pad sections 66, 68. One advantage of employing pads with different sections is that the separate sections may have different characteristics. For example, typically the pads 60 will be folded so that the central section 66 will comprise the facing surface in the sling 20, so that the central section will engage the wearer. One option is to employ an antibacterial or antimicrobial textile fabric, such as fabrics that can include fibers can then be used in knits, wovens or nonwoven fabrics as either a filament or spun yarn. A material incorporating these fabrics can then be used in the central section, or at least the fabric on the exterior of the central pad section 66. Antibacterial fabrics of this type are generally more costly than conventional fluid absorbent fabrics, and their use in only one section will reduce the overall cost of the fluid absorbent pad 60. Alternatively the central section 66 can be quilted to reduce the thickness of this section. The absorbent pad 60*a* shown in FIGS. 9 and 10 has a central quilted section having a rectangular quilt pattern on quilted surface 80. By reducing the thickness of the central section 66, the thickness of the side sections 68 can be greater so that the volume of fluid that can be absorbed can be relatively large without increasing the bulk of the absorbent pad 60*a* to a degree that it would cause discomfort to the wearer. A typical absorbent material for use in side sections 68, as shown in FIGS. 9 and 10 would be a material such as blends of rayon and polyester or viscose or a micro terry fabric including one hundred percent micro terry fabrics.

In some situations, the three layer folding pads may not be sufficient to handle the amount of fluids, especially in localized areas. FIG. 9 shows the use of an additional or auxiliary absorbent pad 67 attached or stitched to a rear surface of the central section 66. In this configuration, that auxiliary pad 67 is shorter than the remainder of the pad 60*a*. As shown in FIG. 9, this auxiliary pad 67 is confined to the area in which most of the fluids for a male would be located, so that auxiliary pad 67 provides additional absorbency in an area of primary need, without the addition of more bulk than would otherwise be necessary. An auxiliary pad 67 for use by a female would be more centered and would not extend from the front edge of the central pad section 66. It should be understood that an additional pad layer, such as that provided by auxiliary pad 67 could be positioned where most needed, and the specific positions discussed herein are representative and not limiting in character. It should also be understood that the auxiliary pad could be attachable to the pad 60*a* and need not be a permanent part of this or any of the other fluid absorbent pads or pad sections discussed herein.

Fluid absorbent materials suitable for use in pads of this type tend to collapse easily and do not retain their shape. This can be a problem when such reusable pads 60 are laundered and it can also be a problem when they bunch up in the groin area when worn. If the sections of these pads are bunched, then they may not be thoroughly cleaned, especially if the sections stick together because of waste deposited on the pads. To provide some structural integrity to the pad sections, overlock stitches 72 are formed along the longitudinal edges of the central section 66 and the side sections 68. Lateral overlock stitches 74 extending along the ends of pad sections 66 and 68. These overlock stitches 72 and/or 74 will provide some peripheral stiffness, without interfering with either the softness or the fluid retention characteristics of the pad sections 66 and 68. When the pads are removed, the peripheral stiffness added by the overlock stitches 72 and 74 will tend to help separate the pad sections to promote more through cleaning, since there will be a greater likelihood that all surfaces will be exposed. Peripherally stiffened pads will also help keep the pads relatively flat against the groin when worn. Overlock stitching is not the only means for providing stiffened peripheral edges that have greater stiffness than central or intermediate portions of the pad section. Alternative means such as the addition of a trim can also be employed, but overlock stitching does have its own advantages.

Figure 11:
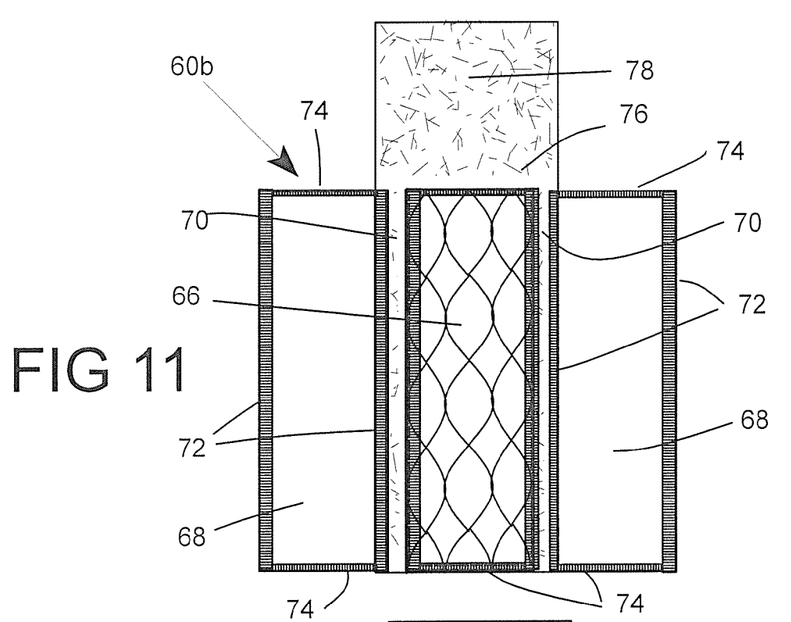
FIGS. 11 and 12 are views of opposite sides of another version of a reusable absorbent pad that can be employed to form the diaper assembly of this invention.
Figure 12:
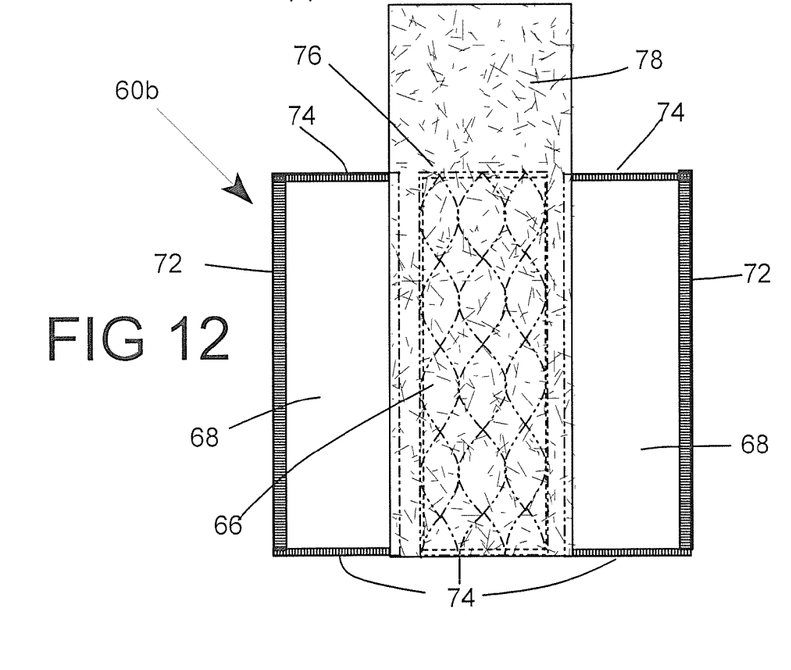

The embodiment of the fluid absorbent pad 60*b*, shown in FIGS. 11 and 12, has the same characteristics as the pad 60*a*, shown in FIGS. 9 and 10. Pad 60*b* has additional feature. The flexible strips 70 of pad 60*b* are part of a sheet 76 that extends across the front surface of the central quilted pad section 66 as shown in FIG. 12. Furthermore the sheet 76 extends beyond one end of the pad 60*b* to form a flap 78. This flap 78 can be folded partially over the central pad section 66 when this folded pad 60*b* is inserted into a sling. The flap 78 will serve as depository of solid waste or excrement, and can be termed a poo catcher. When a soiled pad 60*b* is removed, the flap or poo catcher 78 on which solid waste is deposited can be easily rinsed in a toilet or basin filled with water to remove this solid waste or excrement. The sheet 76 can also be formed of a fluid permeable material, such as stay dry brushed polyester or microfiber fleece, which will allow moisture to wick through this material so that it will remain dryer and thus will cause less irritation to the wearer.

Figure 13:
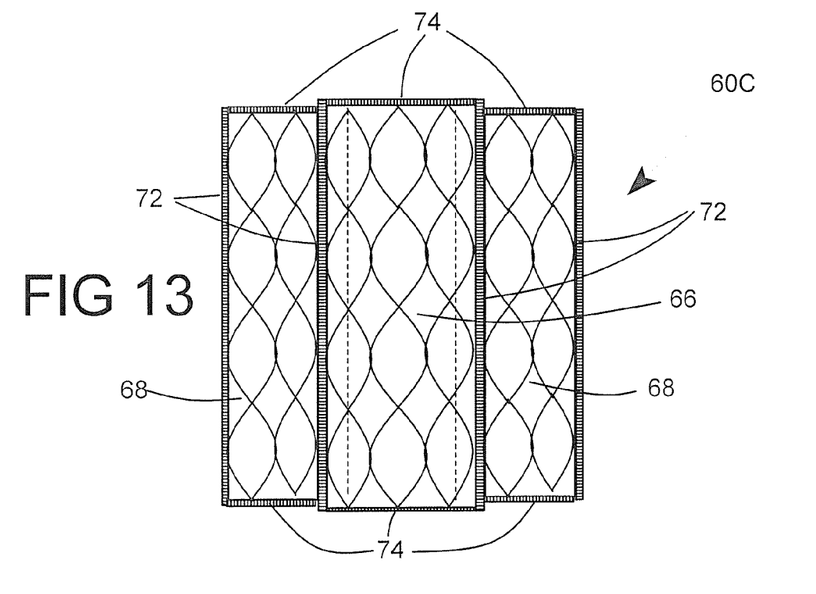
FIGS. 13 and 14 are views of opposite sides of a third version of a reusable absorbent pad that can be employed to form the diaper assembly of this invention.
Figure 14:
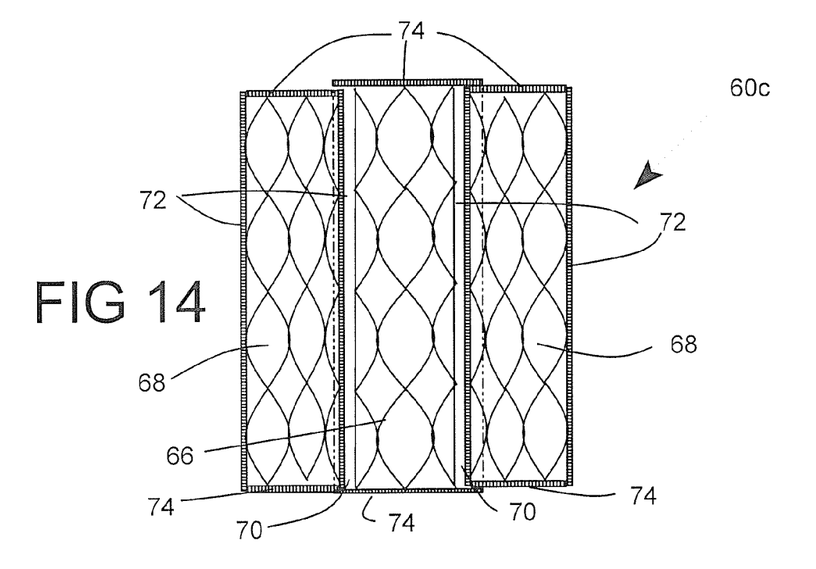
Figure 17:
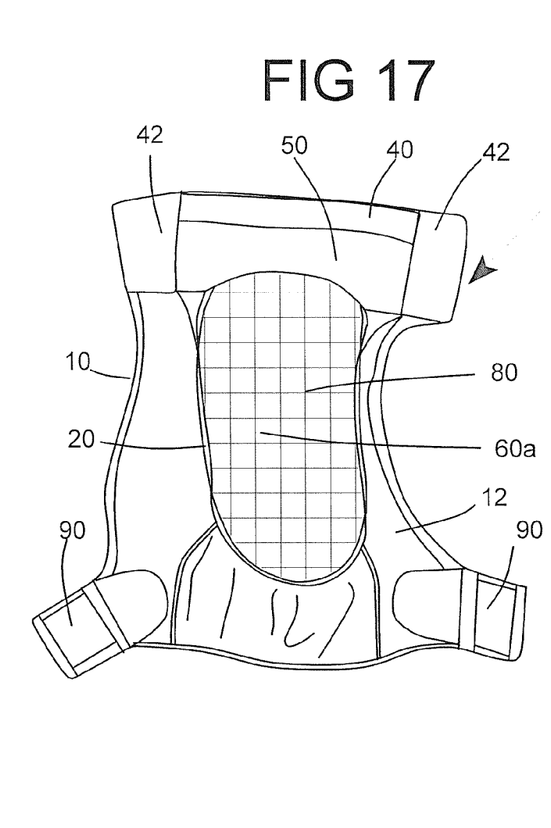
FIG. 17 is a view showing the pad of FIGS. 9 and 10 inserted into the sling in the diaper garment to form the diaper assembly according to this invention.
Figure 18:
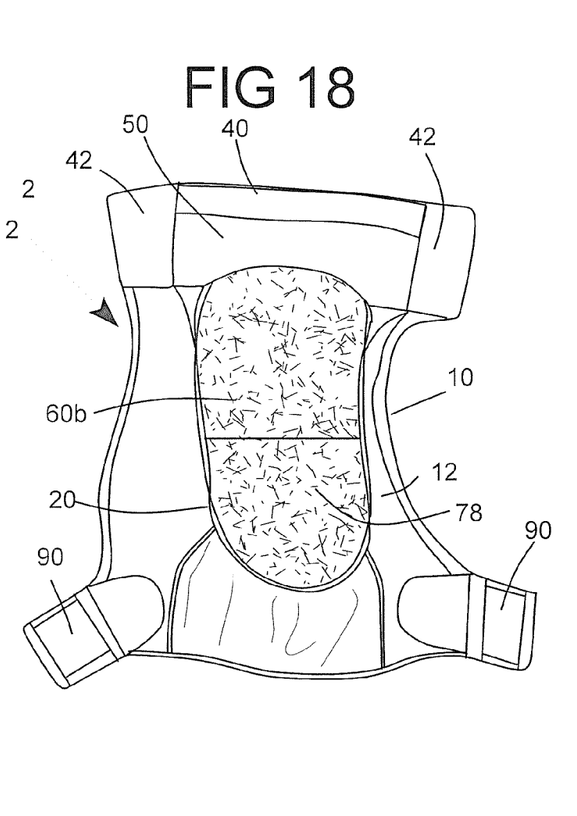
FIG. 18 is a view showing the pad of FIGS. 12 and 13 inserted into the sling in the diaper garment to form the diaper assembly according to this invention.

The foldable, fluid absorbent pad 60*c* shown in FIGS. 13 and 14 has many of the same characteristics as pads 60*a* and 60*b*. This pad 60*c* can be less bulky then these other pads. Note, for example, that all three sections 66, 68 are quilted to reduce bulk. Furthermore, the side sections 68 partially overlap the central pad 66 so that the width of the folded pad can be less than, for example, the pad 60*a*. The reduced width can be more comfortable for use by females or by smaller individuals. In this embodiment, one edge of the flexible strips 70 will be stitched to the central pad section 66, at a location slightly inside of the edges of the central pad section 66. Overlock stitches 72 can still be employed to add desirable peripheral stiffness to this version of a folding, fluid absorbent pad. FIGS. 17 and 18 show the pads 60*a* and 60*b* inserted into the sling 20 to form different versions of the diaper assembly 2. FIG. 3 shows a fluid absorbent pad with a diamond quilted pattern, which can be pad 60*c* of FIGS. 13 and 14, positioned within a sling 20.

Figure 15:
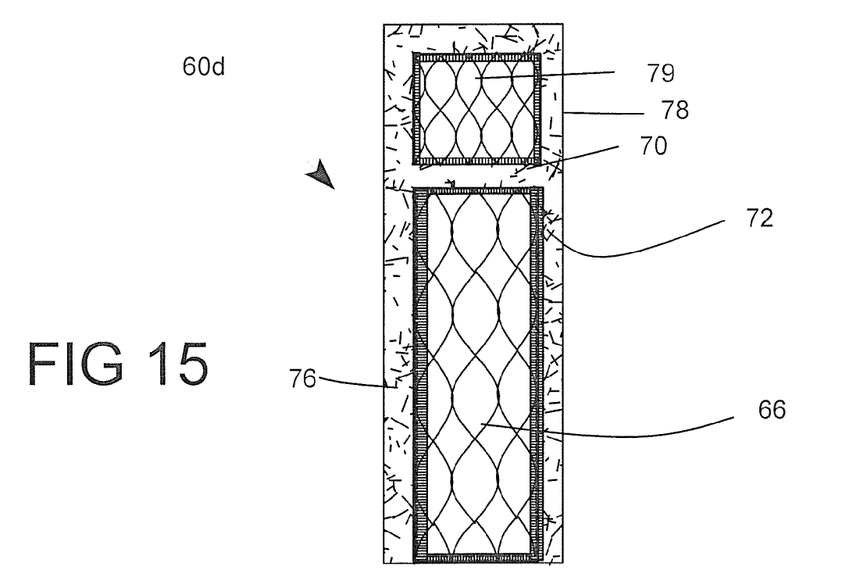
FIGS. 15 and 16 are views of opposite sides of a fourth version of a reusable absorbent pad having only two folding layers that can be employed to form the diaper assembly of this invention.
Figure 16:
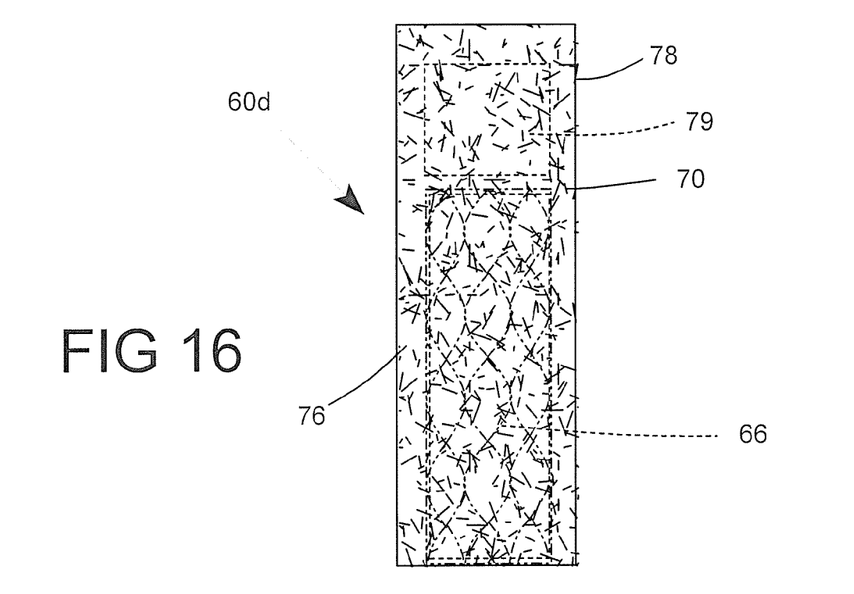

FIGS. 15 and 16 show another version of a folding fluid absorbent pad 60*d*. In this version, only two sections are employed. This version can have less bulk than the three other embodiments, and would suitable where less fluid must be absorbed. A larger fluid absorbent pad 66 is positioned on a main pad section 66, which can be identical to the central pad section of FIGS. 11 and 12. A flap 78 includes a smaller pad 79, and this flap 78 including the smaller pad 79 can be folded down over the larger pad section 66 by folding along an intermediate flexible strip 70 joining the two pad sections. In this embodiment a sheet 76, constructed of the same material employed for the sheet in the embodiment of FIGS. 11 and 12, is employed to both form the flexile strip 70 and for mounting the pads 66 and 79. Since this soft, fluid permeable sheet 76 extends beyond the pads 66 and 79 on all sides, this soft, comfortable material will form a border when the smaller pad 79 is folded under the larger pad 66.

Figure 19A:
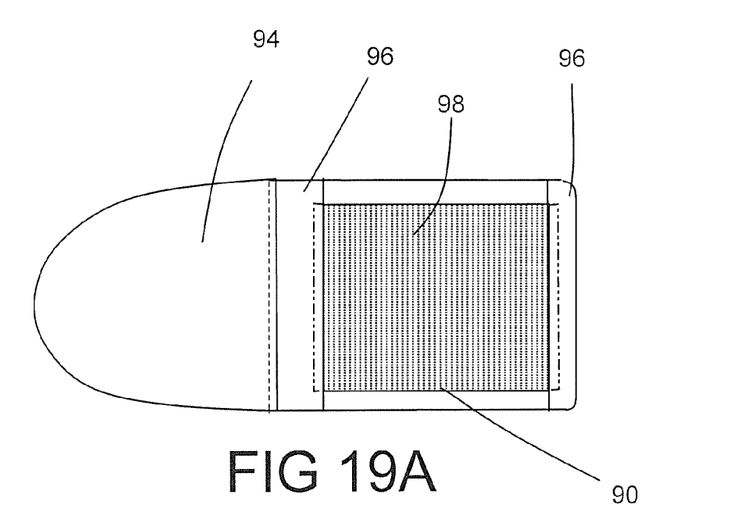
FIG. 19A-19D show the hook fastener tab according to this invention, and significant steps in the fabrication of this hook fastener tab.
Figure 19B:
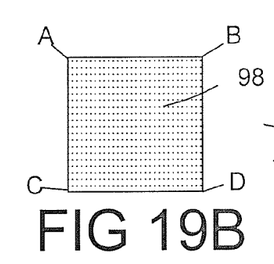
Figure 19C:
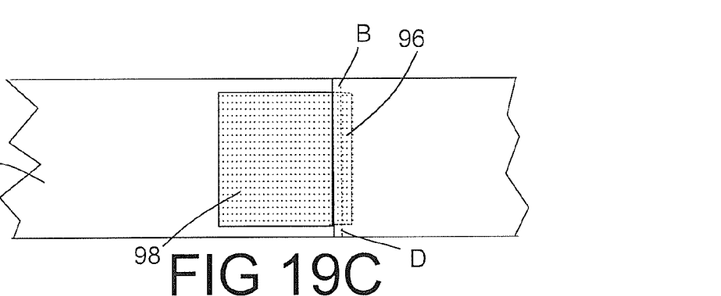
Figure 19D:
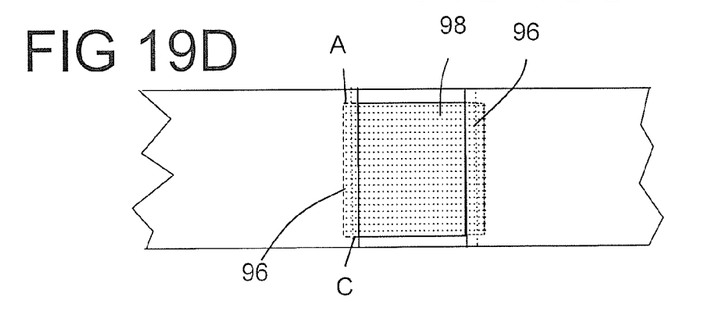

One other possible source of irritation to the wearer of a diaper can be the fasteners that are used to secure a diaper to the person's body. Although hook and loop fasteners can be very convenient and are not very bulky, exposed hook fasteners can scratch irritate the skin of the wearer and can scratch the hands of the person applying the diaper. FIG. 19A shows a hook fastener 90 in which the most likely source of scratching and irritation has been eliminated. It is the exposed corners of a rectangular hook element that can cause the most irritation. FIG. 19B shows a square or rectangular hook material having four corners A, B, C, D. As shown in FIGS. 19C and 19D, the cloth fabric, on which the hook fastener element 98 is mounted, is folded over opposite sides of the hook fastener element 98 to form folds 96. These folds 96 will cover all four corners A, B, C, D so that they will not be exposed to scratch or irritate the wearer on the person diapering the wearer. Further protection can be provided by folding over the third and fourth sides of the cloth backing to cover not only the corners, but also the sides of the hook fastener. Once the fastener 90 has been fabricated to cover the abrasive corners of hook element 98, the cloth backing can be attached or stitched to an auxiliary closing tab 94, which in the preferred embodiment comprises a piece of relatively soft loop material. The hook fastener tab 90 can be folded over to engage this auxiliary closing tab 94 when the diaper garment 10 is to be laundered or cleaned or even during storage of the garment. Sharp hooks will then not be exposed and cannot cause damage to other portions of the diaper garment 10 nor will they be caught on other garments in the laundry. Thus the hook fasteners 90 cannot cause multiple garments to become entangled during cleaning so that the entangled garments, and especially the diaper, will not effectively cleaned.

It should be understood that the embodiments depicted herein are merely representative of a diaper assembly that includes a number of features that enhance the comfort of a diaper. In other embodiments, some of the elements of this invention might be eliminated, and although these alternatives may not be as effective as the preferred embodiments, they still might represent an improvement over existing diapers and diaper assemblies. For example, the diaper garment of FIGS. 1 and 2 could be employed with a single layer pad. Alternatively, the multilayer pads of FIGS. 9-14 could be employed with a diaper garment that did not employ the unique front pocket of the preferred embodiments of this invention. The multilayer pads could also be employed with other undergarments. The materials suggested for use in the preferred embodiments are also not intended to be the only materials that can be employed to construct a diaper or undergarment. Although the preferred embodiment of this invention is intended for use as a diaper assembly, it should be understood that in some respects it can be adapted to other undergarments. For example the sling could be used on a training pant. The sling could also be modified. For example, a shield as well as top and side gussets could be employed at both the front and rear ends of the sling, instead of just at the front end as shown in the preferred embodiments. The invention disclosed herein, is therefore not limited to the representative embodiments depicted herein, but is instead to be interpreted by the following claims.

I claim:

1. A diaper assembly comprising a fluid absorbent pad and a diaper garment, wherein:

the diaper garment comprises an outer shell including fasteners for securing the diaper garment to a wearer and a fluid resistant sling secured at a front end to the outer shell and at a rear end to the outer shell, the sling being free from the outer shell between the front end and the rear end, the fluid absorbent pad being carried by and removable from the fluid resistant sling, and wherein; the sling includes a front pocket and a rear pocket, opposite ends of the fluid absorbent pad being insertable into the front and rear pockets of the sling; and wherein; a rear fabric layer, softer to the touch than the fluid resistant sling, overlays the rear pocket and suspends the sling from the outer shell at a rear sling end, and wherein; a front subassembly comprising two side fabric gussets and top fabric gusset secured to a fluid resistant front shield overlaying the front pocket, the top fabric gusset extends beyond the overall width of the sling, the top fabric gusset is aligned and overlaid on the fluid resistant front shield such that the top and side fabric gussets surround the fluid resistant shield on three sides and conceal a portion of the fluid resistant front shield underneath the front subassembly, the top and side fabric gussets each being formed from a material softer to the touch than the fluid resistant sling and the fluid resistant front shield, the top and side gussets securing the sling at the front end to the outer shell, thereby the top and side fabric gussets in the front subassembly and the rear fabric layer provide comfort when contacting a wearer's skin by reducing direct exposure of the wearer's skin to fluid resistant material.

2. The diaper assembly of claim 1 wherein an anchor stitch extends through the outer shell, the side gussets and the sling at the front end of the sling.

3. The diaper assembly of claim 1 wherein an elastic border extends from one side of the front, fluid resistant shield around the sling to an opposite side of the front, fluid resistant shield but not along a central edge of the front, fluid resistant shield.

4. The diaper assembly of claim 3 wherein the central edge of the front, fluid resistant shield has an arcuate contour.

5. The diaper assembly of claim 4 wherein the arcuate contour is stitched to an arcuate edge of the fluid resistant sling.

6. The diaper assembly of claim 1 wherein front, side edges of the sling are folded over portions of the sling therebetween to extend the front pocket.

7. The diaper assembly of claim 1 wherein the rear single layer comprises a single layer overlaying the rear pocket.

8. The diaper assembly of claim 1 including hook fastener tabs extending from the rear end of the outer shell, the hook fastener tabs including a fabric layer overlying each of four corners of each hook fastener tab.

9. The diaper assembly of claim 1 wherein the absorbent pad comprises a multilayer fabric pad.

10. The diaper assembly of claim 9 wherein the absorbent pad comprise multiple sections joined by a flexible strip so that the multiple sections can be folded over each other.

11. The diaper assembly of claim 10 wherein overlock seams extend along parallel edges of the sections to peripherally stiffen sides of the sections.

12. The diaper assembly of claim 11 wherein the strips comprise portions of a sheet to which three side by side sections are joined, the sheet being fabricated from a skin friendly material.

13. The diaper assembly of claim 12 wherein the absorbent pad includes a flap extending from one end of the absorbent pad, the flap being foldable over an end of the absorbent pad and comprising means for capturing excrement.

14. The diaper assembly of claim 9 wherein only one section of the absorbent pad, which when folded will be in contact with the wearer's skin, is fabricated from an antibacterial fabric.

15. The diaper assembly of claim 1 wherein the absorbent pad comprises a fabric pad having at least one quilted section to reduce bulk.

16. The diaper assembly of claim 1 wherein the absorbent pad comprises three sections joined by flexible sections between the sections, the sections being foldable into overlapping relationship, and wherein a central section is wider than sections on either side to reduce the width of the absorbent pad.

17. The diaper assembly of claim 1, wherein the fluid absorbent pad is fabricated from reusable materials, for use in an undergarment comprising a fluid permeable sheet through which moisture will wick and a plurality of spaced apart fluid absorbent sections attached to the fluid permeable sheet, the fluid permeable sheet being more flexible than the fluid absorbent sections, portions of the fluid permeable sheet between adjacent fluid absorbent sections comprising flexible stripes so that the fluid absorbent pad can be folded into a folded configuration with the fluid permeable sheet at least partially surrounding the fluid absorbent pads so that the fluid permeable sheet will be in contact with a wearer's skin when the pad is used in an undergarment, so that moisture can migrate away from the wearer's skin.

18. A diaper assembly comprising a fluid absorbent pad and a diaper garment,
   the diaper garment comprising an outer shell including fasteners for securing the diaper garment to a wearer and a fluid resistant sling secured at a front end to the outer shell and at a rear end to the outer shell, the sling being free from the outer shell between the front end and the rear end, the sling includes a front pocket and a rear pocket; and
   a front subassembly comprising two side fabric gussets and top fabric gusset secured to a fluid resistant front shield overlaying the front pocket,
   the top fabric gusset extends beyond the overall width of the sling, the top fabric gusset is aligned and overlaid on the fluid resistant front shield such that the top and side fabric gussets surround the fluid resistant shield on three sides and conceal a portion of the fluid resistant front shield underneath the front subassembly,
   the top and side fabric gussets each being formed from a material softer to the touch than the fluid resistant sling and the fluid resistant front shield, the top and side fabric gussets securing the sling at the front end to the outer shell, and
   wherein opposite ends of the fluid absorbent pad are securable within the front and rear pockets of the sling the fluid absorbent pad being carried by and removable from the fluid resistant sling; and
   wherein the fluid absorbent pad comprises a reusable fabric pad having three side by side sections joined by a flexible strip on each side of a central section attaching the central section to sections on each side thereof so that the sections are foldable into overlapping relationship for insertion into the sling, each section of the fluid absorbent pad having an overlock stitch extending along opposite sides between a top and bottom end of the pad, the overlock stitch stiffening each section along opposite sides thereof so that the sections retain their shape when worn to reduce bunching of the fluid absorbent pad in the groin area.

19. The diaper assembly of claim 18 wherein at least one section of the fluid absorbent pad is quilted to reduce bulk.

20. The diaper assembly of claim 18 wherein at least one pad section is formed of an antibacterial fabric.

21. The diaper assembly of claim 18 wherein the three sections are joined by a sheet extending over the central section, the flexible strips comprising opposite sides sections of the sheet, the sheet being formed of a fluid permeable material and each pad section being formed of a fluid absorbent material.

22. The diaper assembly of claim 21 wherein the absorbent pad includes a flap extending from one end of the fluid permeable sheet, the flap being foldable over the end of the absorbent pad and comprising means for capturing excrement.

23. An undergarment for use with a fluid absorbent pad wherein the undergarment comprises an outer shell securable to a wearer and a fluid resistant sling secured at a front end to the outer shell and at a rear end to the outer shell, the sling being free from the outer shell between the front end and the rear end, the sling including a front pocket and a rear pocket for securing opposite ends of the fluid absorbent pad within the front and rear pockets of the sling; the undergarment including a front subassembly positioned on the front end of the outer shell comprising two side fabric gussets and top fabric gusset secured to a fluid resistant front shield overlaying the front pocket,
   the top fabric gusset extends beyond the overall width of the sling, the top fabric gusset is aligned and overlaid on the fluid resistant front shield such that the top and side fabric gussets surround the fluid resistant shield on three sides and conceal a portion of the fluid resistant front shield underneath the front subassembly,
   the top and side fabric gussets each being formed from a material softer to the touch than the fluid resistant sling and the fluid resistant front shield, the top and side gussets securing the sling at the front end to the outer shell, thereby the top and side fabric gussets in the front subassembly and the rear fabric layer provide comfort when contacting a wearer's skin by reducing direct exposure of the wearer's skin to fluid resistant material.

24. The undergarment of claim 23 wherein the undergarment comprises a diaper and wherein the shield and the gussets are located only on a front end of the sling.

25. A fluid absorbent pad for use in an undergarment, wherein the pad comprises a reusable fabric pad having adjacent sections joined by a flexible strip so that the sections are foldable into overlapping relationship for use in the undergarment, each section of the fluid absorbent pad having a stiffened peripheral edge extending along opposite sides between a top and bottom end of the pad, each stiffened peripheral edge having a greater stiffness than central portions of the sections, the stiffened peripheral edge providing stiffness such that the sections retain their shape when worn to reduce bunching of the fluid absorbent pad in the groin area, wherein the stiffened peripheral edge stiffening is formed by an overlook stitch.

26. The fluid absorbent pad of claim 25 wherein the flexible strips are part of a sheet covering one section and joined to at least one other section, the sheet being formed of a fluid permeable material to wick moisture into interior sections of the fluid absorbent pad.

27. The fluid absorbent pad of claim 25 wherein a flap extends from one end of one section, the flap folding over the one section when in use, the flap collecting excrement during use and being foldable away from remaining sections of fluid absorbent pad, so that the excrement can be separately removed by dousing the flap in water.

* * * * *